United States Patent
Kim et al.

(10) Patent No.: US 9,978,974 B2
(45) Date of Patent: May 22, 2018

(54) LIGHT-EMITTING DEVICE

(71) Applicant: Samsung Display Co., Ltd., Yongin-si, Gyeonggi-do (KR)

(72) Inventors: Yisu Kim, Yongin-si (KR); Dongchan Kim, Yongin-si (KR); Byoungduk Lee, Yongin-si (KR); Yoonhyeung Cho, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days. days.

(21) Appl. No.: 15/588,134

(22) Filed: May 5, 2017

(65) Prior Publication Data

US 2018/0047928 A1 Feb. 15, 2018

(30) Foreign Application Priority Data

Aug. 10, 2016 (KR) ........................ 10-2016-0101883

(51) Int. Cl.
| | | |
|---|---|---|
| *H01L 51/50* | (2006.01) | |
| *C07C 211/63* | (2006.01) | |
| *C09K 11/06* | (2006.01) | |
| *H01L 51/00* | (2006.01) | |

(52) U.S. Cl.
CPC ........ *H01L 51/5036* (2013.01); *C07C 211/63* (2013.01); *C09K 11/06* (2013.01); *H01L 51/0077* (2013.01); *H01L 51/502* (2013.01); *C09K 2211/10* (2013.01); *C09K 2211/182* (2013.01)

(58) Field of Classification Search
CPC ............. H01L 51/5036; H01L 51/0077; H01L 51/502; C07C 211/63
See application file for complete search history.

(56) References Cited

U.S. PATENT DOCUMENTS

| | | |
|---|---|---|
| 8,084,934 B2 | 12/2011 | Kim et al. |
| 9,054,330 B2 | 6/2015 | Qian et al. |
| 2016/0056337 A1 | 2/2016 | Chao et al. |
| 2017/0054099 A1 | 2/2017 | Friend et al. |
| 2017/0294607 A1* | 10/2017 | Kim ................... H01L 51/0089 |

FOREIGN PATENT DOCUMENTS

| | | |
|---|---|---|
| JP | 2014-78392 | 5/2014 |
| KR | 10-2006-0114523 | 11/2006 |
| KR | 10-2012-0038472 | 4/2012 |
| KR | 10-2013-0055360 | 5/2013 |
| WO | WO 2015/166006 A1 | 11/2015 |

OTHER PUBLICATIONS

Song, Jizhong, et al. "Quantum Dot Light-Emitting Diodes Based on Inorganic Perovskite Cesium Lead Halides ($CsPbX_3$),", Advanced Materials, 2015, vol. 27, pp. 7162-7167.

* cited by examiner

*Primary Examiner* — Dung Le
(74) *Attorney, Agent, or Firm* — Lewis Roca Rothgerber Christie LLP

(57) ABSTRACT

A light-emitting device is provided. The light emitting device includes a first electrode, second electrode facing the first electrode, and an emission layer between the first electrode and the second electrode. The emission layer includes at least one perovskite compound, a first quantum dot, and a second quantum dot. The first quantum dot and the second quantum dot may be different from each other.

20 Claims, 1 Drawing Sheet

10

| 190 |
|---|
| 170 |
| 150 |
| 130 |
| 110 |

10

| 190 |
|-----|
| 170 |
| 150 |
| 130 |
| 110 |

LIGHT-EMITTING DEVICE

CROSS-REFERENCE TO RELATED APPLICATION

This application claims priority to and the benefit of Korean Patent Application No. 10-2016-0101883, filed on Aug. 10, 2016, in the Korean Intellectual Property Office, the entire content of which is incorporated herein by reference.

BACKGROUND

1. Field

One or more embodiments relate to a light-emitting device

2. Description of the Related Art

Light-emitting devices are devices that convert electrical energy into light energy. Examples of such light-emitting devices may include an organic light-emitting device including an organic material in an emission layer, a quantum dot light-emitting device including a quantum dot in an emission layer, and the like. Due to ambient oxygen or moisture, emission characteristics of these light-emitting devices may be degraded.

SUMMARY

One or more embodiments include a light-emitting device having high efficiency.

Additional aspects of embodiments will be set forth in part in the description which follows and, in part, will be apparent from the description, or may be learned by practice of the presented embodiments.

According to one or more embodiments, a light-emitting device includes:
 a first electrode;
 a second electrode facing the first electrode; and
 an emission layer between the first electrode and the second electrode,
 wherein the emission layer includes at least one perovskite compound represented by Formula 1, a first quantum dot, and a second quantum dot, and
 the first quantum dot and the second quantum dot are different from each other:

$$[A][B][X]_3 \qquad \text{Formula 1}$$

In Formula 1,

A may be at least one monovalent organic cation, at least one monovalent inorganic cation, or any combination thereof, B may be at least one divalent inorganic cation, and X may be at least one monovalent anion.

BRIEF DESCRIPTION OF THE DRAWING

These and/or other aspects will become apparent and more readily appreciated from the following description of the embodiments, taken in conjunction with the accompanying drawing which is a schematic cross-sectional view of a light-emitting device according to an embodiment.

DETAILED DESCRIPTION

A light-emitting device according to an embodiment may include a first electrode, a second electrode facing the first electrode, and an emission layer between the first electrode and the second electrode. Materials having high chemical stability should be used in such light-emitting devices, so that emission characteristics thereof are improved. A perovskite compound is a generic term for materials having a three-dimensional crystal structure related to a $CaTiO_3$ crystal structure (for example, a cubic crystal structure). Since a perovskite compound has a simple structure and excellent chemical stability, a perovskite compound may be suitable for use in various suitable electronic devices, such as a light-emitting device.

The first electrode may be an anode, the second electrode may be a cathode, and the first electrode and the second electrode are described in more detail below.

The emission layer may include at least one perovskite compound represented by Formula 1, a first quantum dot, and a second quantum dot, and the first quantum dot and the second quantum dot may be different from each other:

$$[A][B][X]_3 \qquad \text{Formula 1}$$

A in Formula 1 may be at least one monovalent organic cation, at least one monovalent inorganic cation, or any combination thereof. As used herein, the terms "combination thereof" and "combinations thereof" may refer to a chemical combination (e.g., an alloy or chemical compound), a mixture, or a laminated structure of components.

For example, A may include i) one monovalent organic cation, ii) one monovalent inorganic cation, iii) a combination of two or more different monovalent organic cations, iv) a combination of two or more different monovalent inorganic cations, or v) a combination of a monovalent organic cation and a monovalent inorganic cation.

In one or more embodiments, A in Formula 1 may be $(R_1R_2R_3R_4N)^+$, $(R_1R_2R_3R_4P)^+$, $(R_1R_2R_3R_4As)^+$, $(R_1R_2R_3R_4Sb)^+$, $(R_1R_2N=C(R_3)-NR_4R_5)^+$, a monovalent cation of a substituted or unsubstituted nitrogen-containing 5-membered ring, a monovalent cation of a substituted or unsubstituted nitrogen-containing 6-membered ring, $Li^+$, $Na^+$, $K^+$, $Rb^+$, $Cs^+$, $Fr^+$, or any combination thereof, and $R_1$ to $R_5$, a substituent of the monovalent cation of the substituted nitrogen-containing 5-membered ring, and a substituent of the monovalent cation of the substituted nitrogen-containing 6-membered ring may each independently be selected from hydrogen, deuterium, —F, —Cl, —Br, —I, a hydroxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_6$-$C_{60}$ aryl group, and —N($Q_1$)($Q_2$)($Q_3$), wherein $Q_1$ to $Q_3$ may each independently be selected from hydrogen, deuterium, a hydroxyl group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_6$-$C_{60}$ aryl group.

As used herein, the terms "nitrogen-containing 5-membered ring" and the "nitrogen-containing 6-membered ring" refer to organic cyclic groups having at least one N and at least one C as ring-forming atoms. For example, the "nitrogen-containing 5-membered ring" may be an imidazole, a pyrazole, a thiazole, an oxazole, a pyrrolidine, a pyrroline, a pyrrole, or a triazolyl, and the "nitrogen-containing 6-membered ring" may be a pyridine, a pyridazine, a pyrimidine, a pyrazine, or a piperidine, but embodiments of the present disclosure are not limited thereto.

For example, A in Formula 1 may be $(R_1R_2R_3R_4N)^+$, $(R_1R_2R_3R_4P)^+$, $(R_1R_2R_3R_4As)^+$, $(R_1R_2R_3R_4Sb)^+$, $(R_1R_2N=C(R_3)-NR_4R_5)^+$, a substituted or unsubstituted imidazolium, a substituted or unsubstituted pyridinium, a substituted or unsubstituted pyridazinium, a substituted or unsubstituted pyrimidinium, a substituted or unsubstituted pyrazinium, a substituted or unsubstituted pyrazolium, a substituted or unsubstituted thiazolium, a substituted or unsubstituted oxazolium, a substituted or unsubstituted piperidinium, a substituted or unsubstituted pyrrolidinium, a substituted or unsubstituted pyrrolinium, a substituted or unsubstituted pyrrolium, a substituted or unsubstituted triazolium, $Li^+$, $Na^+$, $K^+$, $Rb^+$, $Cs^+$, $Fr^+$, or any combination thereof, and $R_1$ to $R_5$, a substituent of the substituted imidazolium, a substituent of the substituted pyridinium, a substituent of the substituted pyridazinium, a substituent of the substituted pyrimidinium, a substituent of the substituted pyrazinium, a substituent of the substituted pyrazolium, a substituent of the substituted thiazolium, a substituent of the substituted oxazolium, a substituent of the substituted piperidinium, a substituent of the substituted pyrrolidinium, a substituent of the substituted pyrrolinium, a substituent of the substituted pyrrolium, and a substituent of the substituted triazolium may each independently be selected from:

hydrogen, deuterium, —F, —Cl, —Br, —I, a hydroxyl group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, and a hydroxyl group;

a phenyl group, a naphthyl group, a biphenyl group, and a terphenyl group;

a phenyl group, a naphthyl group, a biphenyl group, and a terphenyl group, each substituted with at least one selected from deuterium, —F, —Cl, —Br, —I, a hydroxyl group, a $C_1$-$C_{20}$ alkyl group, and a $C_1$-$C_{20}$ alkoxy group; and

—N($Q_1$)($Q_2$)($Q_3$), wherein $Q_1$ to $Q_3$ may each independently be selected from hydrogen, deuterium, a hydroxyl group, a $C_1$-$C_{20}$ alkyl group, a $C_1$-$C_{20}$ alkoxy group, a phenyl group, a naphthyl group, a biphenyl group, and a terphenyl group, but embodiments of the present disclosure are not limited thereto.

In one or more embodiments, A in Formula 1 may be $(R_1R_2R_3R_4N)^+$, $(R_1R_2R_3R_4P)^+$, $(R_1R_2R_3R_4As)^+$, $(R_1R_2R_3R_4Sb)^+$, or any combination thereof, and $R_1$ to $R_4$ may each independently be selected from hydrogen, deuterium, —F, —Cl, —Br, —I, a hydroxyl group, a $C_1$-$C_{20}$ alkyl group, a $C_1$-$C_{20}$ alkoxy group, and —N($Q_1$)($Q_2$)($Q_3$), wherein $Q_1$ to $Q_3$ may each independently be selected from hydrogen, deuterium, a hydroxyl group, a $C_1$-$C_{20}$ alkyl group, and a $C_1$-$C_{20}$ alkoxy group.

In one or more embodiments, A in Formula 1 may be $(R_1R_2R_3R_4N)^+$.

In one or more embodiments, A in Formula 1 may be $(CH_3NH_3)^+$, $(C_2H_6PH_2)^+$, $(CH_3AsH_3)^+$, $(NH_4)^+$, $(CH_3SbH_3)^+$, $(PH_4)^+$, $(PF_4)^+$, $(CH_3PH_3)^+$, $(SbH_4)^+$, $(AsH_4)^+$, $(NCl_4)^+$, $(NH_3OH)^+$, $(NH_3NH_2)^+$, $(CH(NH_2)_2)^+$, $(C_3N_2H_5)^+$, $((CH_3)_2NH_2)^+$, $(NC_4H_8)^+$, $((CH_3CH_2)NH_3)^+$, $((NH_2)_3C)^+$, or any combination thereof, but embodiments of the present disclosure are not limited thereto.

B in Formula 1 may be at least one divalent inorganic cation.

For example, B may be i) one divalent inorganic cation, or ii) a combination of two or more different divalent inorganic cations.

In one or more embodiments, B in Formula 1 may be a divalent cation of a rare earth metal, a divalent cation of an alkaline earth metal, a divalent cation of a late transition metal, or any combination thereof.

In one or more embodiments, B in Formula 1 may be $La^{2+}$, $Ce^{2+}$, $Pr^{2+}$, $Nd^{2+}$, $Pm^{2+}$, $Eu^{2+}$, $Gd^{2+}$, $Tb^{2+}$, $Ho^{2+}$, $Er^{2+}$, $Tm^{2+}$, $Yb^{2+}$, $Lu^{2+}$, $Be^{2+}$, $Mg^{2+}$, $Ca^{2+}$, $Sr^{2+}$, $Ba^{2+}$, $Ra^{2+}$, $Pb^{2+}$, $Sn^{2+}$, or any combination thereof.

In one or more embodiments, B in Formula 1 may be $Eu^{+2}$, but embodiments of the present disclosure are not limited thereto.

X in Formula 1 may be at least one monovalent anion.

For example, X in Formula 1 may be i) one monovalent anion, or ii) a combination of two or more different monovalent anions.

In one or more embodiments, X in Formula 1 may be one halide anion (for example, $F^-$, $Cl^-$, $Br^-$, or $I^-$).

For example, X in Formula 1 may be i) one halide anion, or ii) a combination of two or more different halide anions.

In one or more embodiments, X in Formula 1 may be $I^-$, but embodiments of the present disclosure are not limited thereto.

For example, the perovskite compound represented by Formula 1 may be $(CH_3NH_3)EuI_3$, $KEuI_3$, $RbEuI_3$, or $CsEuI_3$. In one or more embodiments, the perovskite compound represented by Formula 1 may be $(CH_3NH_3)EuI_3$, but embodiments of the present disclosure are not limited thereto.

Goldschmidt's tolerance factor (e.g., a structural index of perovskite) of the perovskite compound represented by Formula 1 is substantially about 1 (for example, tolerance factor of $(CH_3NH_3)EuI_3$=about 0.917). Thus, the perovskite compound represented by Formula 1 may have high structural stability.

Accordingly, for example, an emission layer including the perovskite compound represented by Formula 1 may have high quantum efficiency (PLQY) and a narrow full width at half maximum (FWHM), and a light-emitting device including the perovskite compound represented by Formula 1 may have excellent efficiency (e.g., external quantum efficiency, light efficiency, and the like), a long lifespan, and high color purity.

The first quantum dot and the second quantum dot are particles with a crystal structure having a size of several to tens of nanometers and including hundreds to thousands of atoms. Since the first quantum dot and the second quantum dot are very small in size, a quantum confinement effect is exhibited. The quantum confinement effect refers to a phenomenon whereby a band gap of an object increases when a size of the object becomes smaller than a nanoscale size. Accordingly, when light of a wavelength having energy higher than a band gap of the first quantum dot and the second quantum dot is irradiated on the first quantum dot and the second quantum dot, the first quantum dot and the second quantum dot absorb the light and reach an excited state, and then emit light of a set of range of wavelengths (e.g., a specific wavelength) and fall to a ground state. At this time, the wavelength (or range of wavelengths) of the emitted light has a value corresponding to the band gap.

The first quantum dot and the second quantum dot may each independently include a group II-VI element-containing compound semiconductor nanocrystal, a group III-V element-containing compound semiconductor nanocrystal, a group I-III-V element-containing compound semiconductor nanocrystal, a group I-II-III-V element-containing compound semiconductor nanocrystal, a group II-VI element-containing compound semiconductor nanocrystal doped with a rare earth element or a transition metal element, or any combination thereof.

In one or more embodiments, the first quantum dot may have a core-shell structure that includes a core including a first semiconductor nanocrystal and a shell at least partially surrounding the core and including a second semiconductor nanocrystal, and the second quantum dot may have a core-shell structure that includes a core including a third semiconductor nanocrystal and a shell at least partially surrounding the core and including a fourth semiconductor nanocrystal.

The first semiconductor nanocrystal, the second semiconductor nanocrystal, the third semiconductor nanocrystal, and the fourth semiconductor nanocrystal may each independently include a group II-VI element-containing compound semiconductor nanocrystal, a group III-V element-containing compound semiconductor nanocrystal, a group I-III-V element-containing compound semiconductor nanocrystal, a group V element-containing compound semiconductor nanocrystal, a group II-VI element-containing compound semiconductor nanocrystal doped with a rare earth element or a transition metal element, or any combination thereof.

For example, the group II-VI element-containing compound semiconductor nanocrystal may include ZnS, ZnSe, ZnTe, HgS, HgSe, HgTe, ZnSeS, ZnSeTe, ZnSTe, HgSeS, HgSeTe, HgSTe, HgZnS, HgZnSe, HgZnTe, HgZnSeS, HgZnSeTe, HgZnSTe, or any combination thereof, the group III-V element-containing compound semiconductor nanocrystal may include GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, InAlPAs, or any combination thereof, the group I-III-V element-containing compound semiconductor nanocrystal may include $CuInS_2$, $CuInSe_2$, or any combination thereof, the group I-II-III-V element-containing compound semiconductor nanocrystal may include ZnCuInS, and the group II-VI element-containing compound semiconductor nanocrystal doped with the rare earth element or the transition metal element may include Mn-doped ZnSe (Mn:ZnSe), Cu-doped ZnSe (Mn:ZnSe), Mn-doped ZnTe (Cu:ZnTe), Cu-doped ZnTe (Cu:ZnTe), or any combination thereof.

In one or more embodiments, the first semiconductor nanocrystal may include InP having a grain size of greater than about 3.5 nm and less than or equal to about 15 nm, $CuInS_2$ having a Cu-to-In atomic ratio of about 2:5 to about 8:5, ZnCuInS having a grain size of about 5 nm to about 10 nm, Mn-doped ZnSe (Mn:ZnSe)/ZnS, Mn-doped ZnTe (Mn:ZnTe), or any combination thereof, and the third semiconductor nanocrystal may include InP having a grain size of about 2 nm to about 3.5 nm, $CuInS_2$ having a Cu-to-In atomic ratio of about 0.5:5 to about 2:5, ZnCuInS having a grain size of about 2 nm to about 5 nm, Cu-doped ZnSe (Cu:ZnSe), Cu-doped ZnTe (Cu:ZnTe), or any combination thereof, and the second semiconductor nanocrystal and the fourth semiconductor nanocrystal may each independently include ZnS.

In some embodiments, the first quantum dot and the second quantum dot are substantially free (or completely free) of Cd. As used, herein the expression "substantially free of Cd" means that Cd is only present, if at all, as an incidental impurity. Since the first quantum dot and the second quantum dot do not include Cd as a component of the core and/or the shell, a light-emitting device including the first quantum dot and the second quantum dot hardly emits toxic materials during manufacturing and driving. Also, the light-emitting device may have excellent stability and may have excellent efficiency (e.g., external quantum efficiency, light efficiency, and the like), a long lifespan, and high color purity.

In one or more embodiments, the perovskite compound may emit first color light, the first quantum dot may emit second color light, and the second quantum dot may emit third color light, an upper (e.g., maximum) emission wavelength of the first color light, an upper (e.g., maximum) emission wavelength of the second color light, and an upper (e.g., maximum) emission wavelength of the third color light may be identical to or different from one another, and mixed light including the first color light, the second color light, and the third color light may be emitted.

In one or more embodiments, the upper (e.g., maximum) emission wavelength of the first color light, the upper (e.g., maximum) wavelength of the second color light, and the upper (e.g., maximum) wavelength of the third color light may be different from one another, and mixed light including the first color light, the second color light, and the third color light may be white light, but embodiments of the present disclosure are not limited thereto.

In one or more embodiments, the first color light may be blue light, the second color light may be red light, and the third color light may be green light. For example, the perovskite compound may emit blue light, the first quantum dot may emit red light, and the second quantum dot may emit green light.

The perovskite compound, the first quantum dot, and the second quantum dot are included in the emission layer, and have crystal structures capable of effectively confining each exciton. Accordingly, the quantum efficiency of the perovskite compound, the first quantum dot, and the second quantum dot is high, and when a device is manufactured using the same, the device may have high efficiency.

The light-emitting device may further include at least one of a hole transport region between the first electrode and the emission layer; and an electron transport region between the emission layer and the second electrode, wherein at least one of the hole transport region and the electron transport region of the light-emitting device may include an inorganic material.

For example, at least one of the hole transport region and the electron transport region of the light-emitting device may independently include a metal halide, a metal oxide, a metal chalcogenide, a metal selenide, or any combination thereof.

In one or more embodiments, at least one of the hole transport region and the electron transport region may independently include:

a group IV element-containing compound semiconductor (for example, silicon carbide);

a group III-V element-containing compound semiconductor (for example, gallium arsenide);

a group II-VI element-containing compound semiconductor (for example, cadmium selenide);

a group I-VII element-containing compound semiconductor (for example, copper(I) chloride or CuI);

a group IV-VI element-containing compound semiconductor (for example, lead selenide);

a group V-VI element-containing compound semiconductor (for example, bismuth telluride);

a group II-V element-containing compound semiconductor (for example, cadmium arsenide);

a ternary or quaternary compound semiconductor (for example, copper indium selenide, copper indium gallium diselenide, copper zinc tin sulfide, or copper zinc tin sulfide selenide (CZTSSe)); or any combination thereof, but embodiments of the present disclosure are not limited thereto.

For example, at least one of the hole transport region and the electron transport region of the light-emitting device may independently include:

a halide (for example, fluoride, chloride, bromide, iodide, or the like) of iron, silver, copper, cadmium, manganese, cobalt, nickel, mercury, or zinc, or any combination thereof (for example, an alloy or the like);

an oxide of titanium, niobium, tin, zinc, cadmium, copper, lead, molybdenum, nickel, chromium, or tungsten, or any combination thereof (for example, an alloy or the like);

a chalcogenide (for example, copper sulfide or iron sulfide) of antimony, copper, zinc, iron, or bismuth, or any combination thereof (for example, an alloy or the like);

a copper zinc tin chalcogenide (for example, a copper zinc tin sulfide such as $Cu_2ZnSnS_4$ (CZTS) and a copper zinc tin sulfur selenide such as $Cu_2ZnSn(S_{1-x}Se_x)_4$ (CZTSSe));

a copper indium chalcogenide such as copper indium selenide (CIS);

a copper indium gallium selenide such as copper indium gallium selenide ($CuIn_{1-x}Ga_xSe_2$) (CIGS);

a copper indium gallium diselenide; or any combination thereof, but embodiments of the present disclosure are not limited thereto. In some embodiments, x may be a real number greater than 0 and less than or equal to 1.

In one or more embodiments, at least one of the hole transport region and the electron transport region may include an organic material.

In one or more embodiments, the hole transport region may include an amine-based compound, or the electron transport region may include a metal-free compound including at least one π electron-depleted nitrogen-containing ring, but embodiments of the present disclosure are not limited thereto.

Organic materials and additional materials, which may be included in the hole transport region and the electron transport region, are the same as described below.

Description of the Accompanying Drawing

The accompanying drawing is a schematic view of a light-emitting device 10 according to an embodiment. The light-emitting device 10 includes a first electrode 110, a hole transport region 130, an organic layer 150, an electron transport region 170, and a second electrode 190.

Hereinafter, the structure of the light-emitting device 10 according to an embodiment and a method of manufacturing the light-emitting device 10 will be described in connection with the accompanying drawing.

[First Electrode 110]

In the accompanying drawing, a substrate may be additionally disposed under the first electrode 110 or above the second electrode 190. The substrate may be a glass substrate or a plastic substrate, each having, for example, excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode may be selected from materials having a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but embodiments of the present disclosure are not limited thereto. When the first electrode 110 is a semi-transmissive electrode or a reflective electrode, as a material for forming the first electrode 110, magnesium (Mg), silver (Ag), aluminum (Al), aluminum-lithium (Al—Li), calcium (Ca), magnesium-indium (Mg—In), magnesium-silver (Mg—Ag), or any combination thereof may be used. However, the material for forming the first electrode 110 is not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

[Hole Transport Region 130]

The hole transport region 130 may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer (HIL), a hole transport layer (HTL), an emission auxiliary layer, and an electron blocking layer (EBL).

For example, the hole transport region may have a single-layered structure including a single layer including one (e.g., a single or sole) material (for example, the hole transport region includes a hole transport layer including one material), a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include an inorganic material described above.

In one or more embodiments, the hole transport region may include an organic material.

Examples of the organic material include m-MTDATA, TDATA, 2-TNATA, NPB (NPD), β-NPB, TPD, spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate (PANI/PSS), poly[(9,9-dioctylfluorenyl-2,7-diyl)-co-(4,4-(N-(4-sec-butylphenyl)diphenylamine)] (TFB), poly(N,N'-bis(4-butylphenyl)-N,N'-bis(phenyl)benzidine (poly-TPD), and poly-n-vinylcarbazole (PVK).

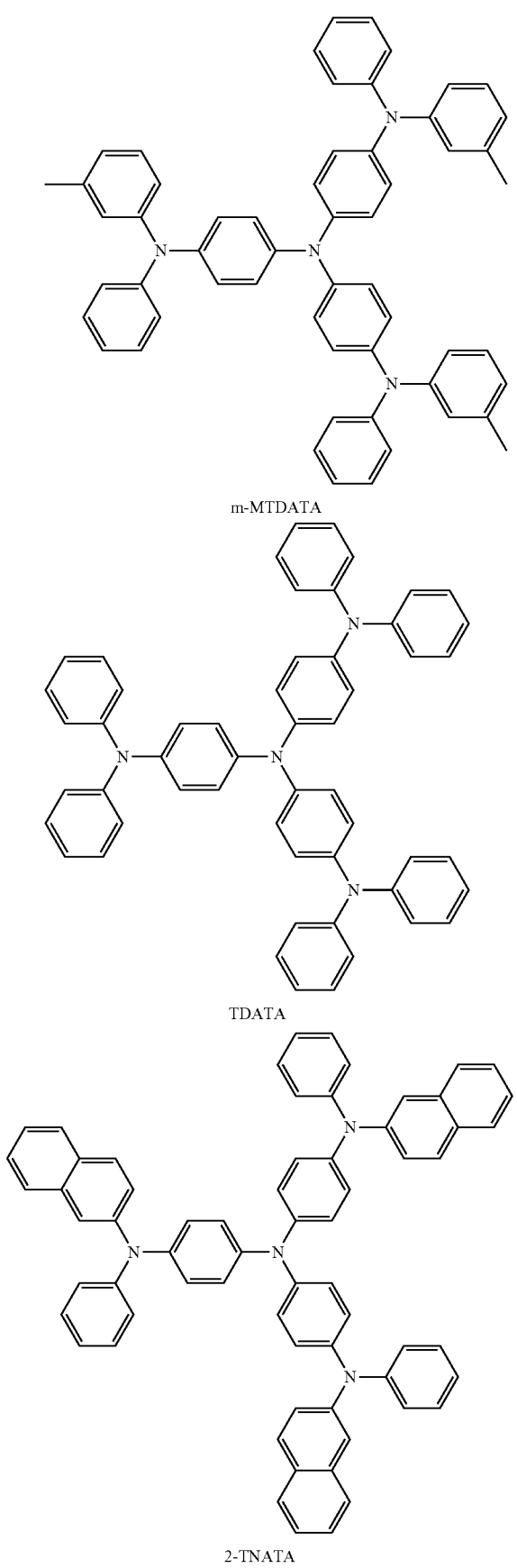
m-MTDATA
TDATA
2-TNATA
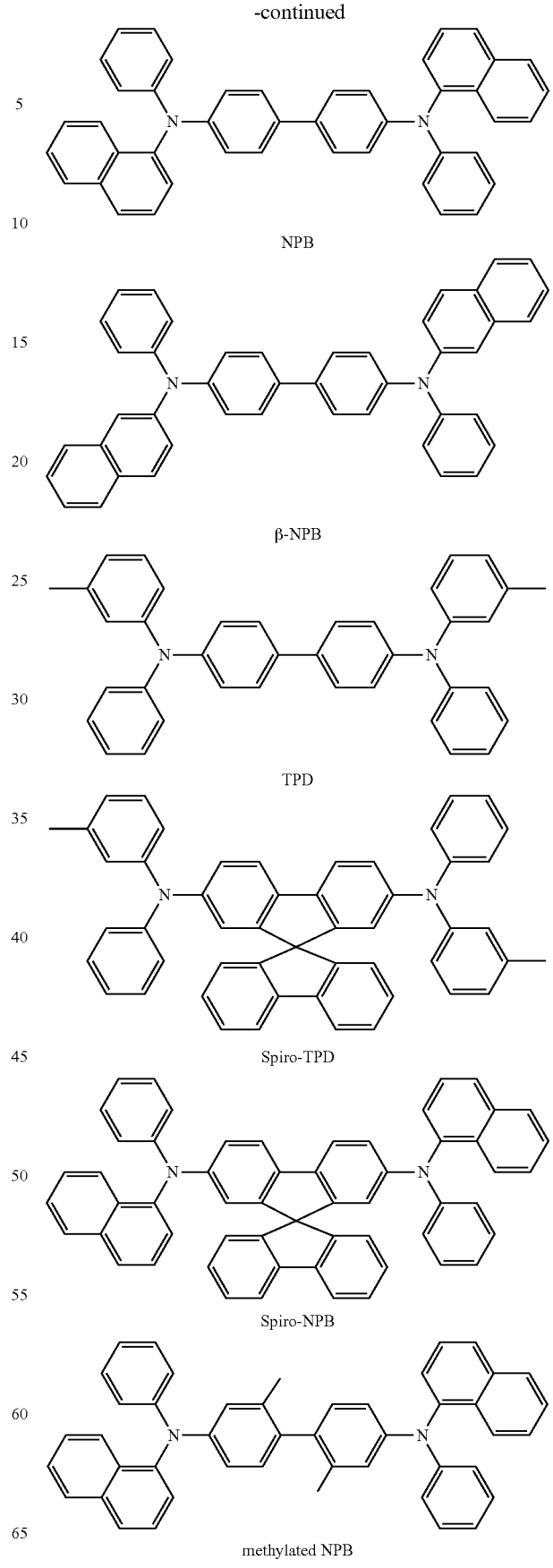
NPB
β-NPB
TPD
Spiro-TPD
Spiro-NPB
methylated NPB

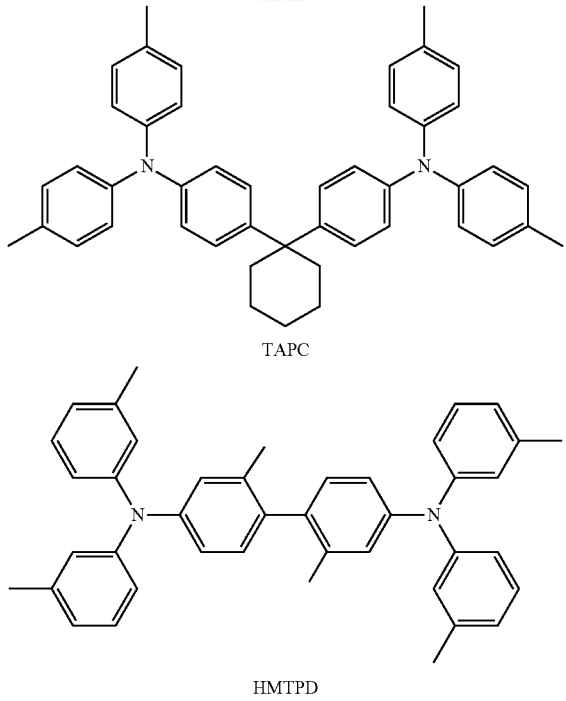

TAPC

HMTPD

In one or more embodiments, an example of the organic material is an amine-based compound.

For example, the hole transport region may include at least one selected from a compound represented by Formula 201 and a compound represented by Formula 202.

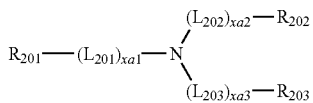
Formula 201

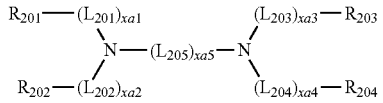
Formula 202

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer of 1 to 10, $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one or more embodiments, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one or more embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group;

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si$(Q_{31})(Q_{32})(Q_{33})$, and —N$(Q_{31})(Q_{32})$, and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and apyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si$(Q_{31})(Q_{32})(Q_{33})$, and —N$(Q_{31})(Q_{32})$, and $Q_{31}$ to $Q_{33}$ may be the same as described above.

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer and the hole transport layer are within any of the foregoing ranges, suitable or satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include any of the suitable materials described above.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one or more embodiments, a lowest unoccupied molecular orbital (LUMO) of the p-dopant may be −3.5 eV or less.

The p-dopant may include at least one selected from a quinone derivative, a metal oxide, and a cyano group-containing compound, but embodiments of the present disclosure are not limited thereto.

For example, the p-dopant may include at least one selected from:

a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and a compound represented by Formula 221 below:

but embodiments of the present disclosure are not limited thereto:

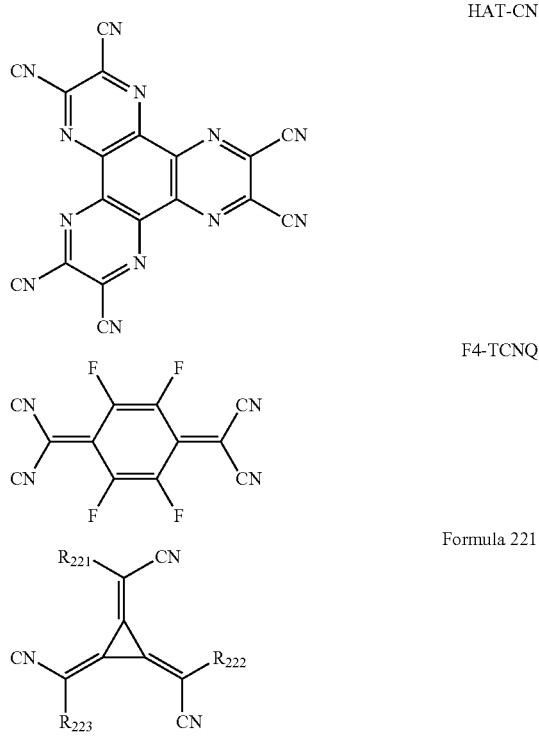

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group, wherein at least one of $R_{221}$ to $R_{223}$ may include at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer 150]

The emission layer 150 may include a perovskite compound represented by Formula 1. Methods of forming the emission layer 150 may be understood by referring to a method of forming a thin film including the perovskite compound described herein.

A thickness of the emission layer 150 may be in a range of about 100 Å to about 1,000 Å, for example, about 200 Å to about 600 Å. When the thickness of the emission layer 150 is within any of the foregoing ranges, excellent light-emission characteristics may be obtained without a substantial increase in driving voltage.

[Electron Transport Region 170]

The electron transport region 170 may have i) a single-layered structure including a single layer including a single (or sole) material, ii) a single-layered structure including a single layer including a plurality of different materials, or iii) a multi-layered structure having a plurality of layers including a plurality of different materials.

The electron transport region 170 may include at least one selected from a buffer layer, a hole blocking layer, an electron control layer, an electron transport layer, and an electron injection layer, but embodiments of the present disclosure are not limited thereto.

For example, the electron transport region 170 may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from the emission layer 150. However, embodiments of the structure of the electron transport region are not limited thereto.

The electron transport region 170 may include an inorganic material. The inorganic material may be the same as described above.

In one or more embodiments, the electron transport region 170 may include the perovskite compound represented by Formula 1.

In one or more embodiments, the electron transport region 170 may include an organic material.

The organic material included in the electron transport region 170 may be a metal-free compound having at least one π electron-depleted nitrogen-containing ring.

The "π electron-depleted nitrogen-containing ring" indicates a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but embodiments of the present disclosure are not limited thereto.

For example, the electron transport region 170 may include a compound represented by Formula 601:

$[Ar_{601}]_{xe11}-[(L_{601})_{xe1}-R_{601}]_{xe21}.$  Formula 601

In Formula 601,

Ar$_{601}$ may be a substituted or unsubstituted C$_5$-C$_{60}$ carbocyclic group or a substituted or unsubstituted C$_1$-C$_{60}$ heterocyclic group, xe11 may be 1, 2, or 3, L$_{601}$ may be selected from a substituted or unsubstituted C$_3$-C$_{10}$ cycloalkylene group, a substituted or unsubstituted C$_1$-C$_{10}$ heterocycloalkylene group, a substituted or unsubstituted C$_3$-C$_{10}$ cycloalkenylene group, a substituted or unsubstituted C$_1$-C$_{10}$ heterocycloalkenylene group, a substituted or unsubstituted C$_6$-C$_{60}$ arylene group, a substituted or unsubstituted C$_1$-C$_{60}$ heteroarylene group, a substituted or unsubstituted divalent non-aromatic condensed polycyclic group, and a substituted or unsubstituted divalent non-aromatic condensed heteropolycyclic group;

xe1 may be an integer selected from 0 to 5,

R$_{601}$ may be selected from a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —Si(Q$_{601}$)(Q$_{602}$)(Q$_{603}$), —C(=O)(Q$_{601}$), —S(=O)$_2$(Q$_{601}$), and —P(=O)(Q$_{601}$)(Q$_{602}$), Q$_{601}$ to Q$_{603}$ may each independently be a C$_1$-C$_{10}$ alkyl group, a C$_1$-C$_{10}$ alkoxy group, a phenyl group, a biphenyl group, a terphenyl group, or a naphthyl group, xe21 may be an integer selected from 1 to 5.

In one or more embodiments, at least one of Ar$_{601}$(s) in the number of xe11 and/or at least one of R$_{601}$(s) in the number of xe21 may include the π electron-depleted nitrogen-containing ring.

In one or more embodiments, ring Ar$_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an aza carbazole group;

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, phenanthroline group, phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an aza carbazole group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, —Si(Q$_{31}$)(Q$_{32}$)(Q$_{33}$), —S(=O)$_2$(Q$_{31}$) and —P(=O)(Q$_{31}$)(Q$_{32}$), and Q$_{31}$ to Q$_{33}$ may each independently be selected from a C$_1$-C$_{10}$ alkyl group, a C$_1$-C$_{10}$ alkoxy group, a phenyl group, a biphenyl group, a terphenyl group, and a naphthyl group.

When xe11 in Formula 601 is two or more, two or more Ar$_{601}$(s) may be linked to each other via a single bond.

In one or more embodiments, L$_{601}$ and L$_{611}$ to L$_{613}$ in Formula 601 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

but embodiments of the present disclosure are not limited thereto.

In one or more embodiments, xe1 and xe611 to xe613 in Formula 601 may each independently be 0, 1, or 2.

In one or more embodiments, $R_{601}$ and $R_{611}$ to $R_{613}$ in Formula 601 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

—S(=O)$_2$(Q$_{601}$), and —P(=O)(Q$_{601}$)(Q$_{602}$); and

Q$_{601}$ and Q$_{602}$ may be the same as described above.

In one or more embodiments, the electron transport region 170 may include at least one compound selected from 2,9-dimethyl-4,7-diphenyl-1,10-phenanthroline (BCP), 4,7- diphenyl-1,10-phenanthroline (Bphen), Alq₃, BAlq, TAZ (3-(biphenyl-4-yl)-5-(4-tert-butylphenyl)-4-phenyl-4H-1,2,4-triazole), NTAZ, and TPBi, but embodiments of the present disclosure are not limited thereto.

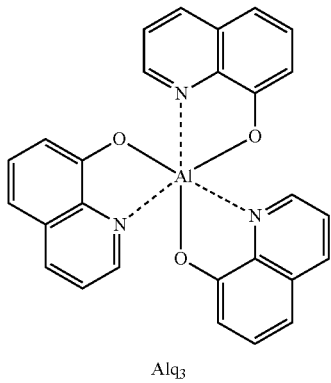

Alq₃

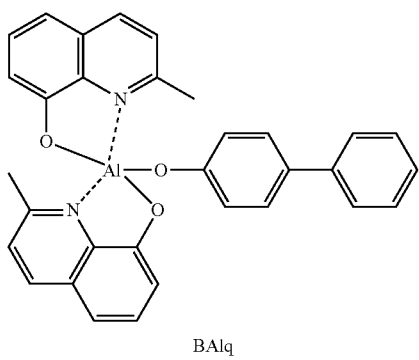

BAlq

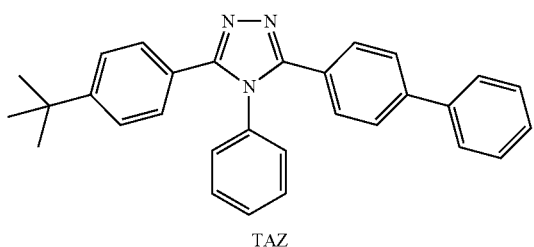

TAZ

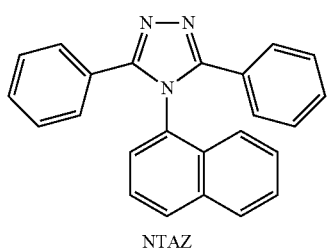

NTAZ

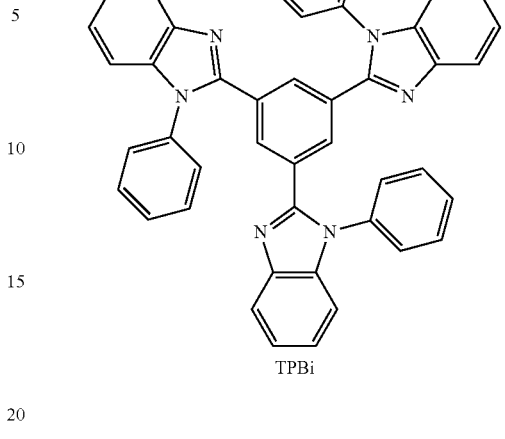

TPBi

A thickness of the electron transport layer may be in a range of about 100 Å to about 1,000 Å, for example, about 150 Å to about 700 Å. When the thickness of the electron transport layer is within any of the ranges described above, the electron transport layer may have suitable or satisfactory electron transport characteristics without a substantial increase in driving voltage.

The electron transport region 170 (for example, an electron transport layer in the electron transport region) may further include a metal-containing material, in addition to the materials described above.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenylan oxazole, a hydroxy phenylthiazole, a hydroxy diphenylan oxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2.

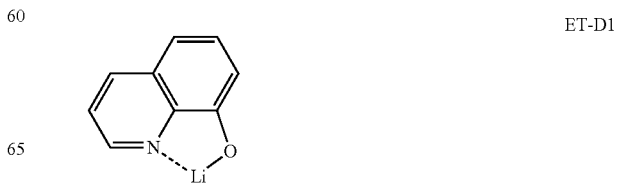

ET-D1

-continued

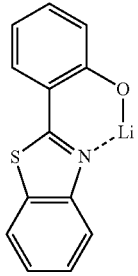
ET-D2

The electron transport region 170 may include an electron injection layer that facilitates injection of electrons from the second electrode 190. The electron injection layer may directly contact the second electrode 190.

The electron injection layer may have i) a single-layered structure including a single layer including a single (or sole) material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs.

The alkaline earth metal may be selected from Mg, Ca, Sr, and Ba.

The rare earth metal may be selected from Sc, Y, Ce, Yb, Gd, and Tb.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, KI, or RbI. In one or more embodiments, the alkali metal compound may be selected from LiF, $Li_2O$, NaF, LiI, NaI, CsI, KI, and RbI, but embodiments of the present disclosure are not limited thereto.

The alkaline earth-metal compound may be selected from alkaline earth-metal compounds, such as BaO, SrO, CaO, $Ba_xSr_{1-x}O$ (0<x<1), $Ba_xCa_{1-x}O$ (0<x<1). In one or more embodiments, the alkaline earth-metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$, and $TbF_3$. In one or more embodiments, the rare earth metal compound may be selected from $YbF_3$, $ScF_3$, $TbF_3$, $YbI_3$, $ScI_3$, and $TbI_3$, but embodiments of the present disclosure are not limited thereto.

For example, the electron injection layer may include an alkali metal compound (for example, RbI or the like) and a rare earth metal (for example, Yb), but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenylan oxazole, hydroxy phenylthiazole, hydroxy diphenylan oxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within any of the ranges described above, the electron injection layer may have suitable or satisfactory electron injection characteristics without a substantial increase in driving voltage.

[Second Electrode 190]

The second electrode 190 may be disposed on the electron transport layer 170 having such a structure. The second electrode 190 may be a cathode which is an electron injection electrode, and in this regard, a material for forming the second electrode 190 may be selected from a metal, an alloy, an electrically conductive compound, and a combination thereof, which have a relatively low work function.

The second electrode 190 may include at least one selected from lithium (Li), silver (Si), magnesium (Mg), aluminum (Al), aluminum-lithium (Al—Li), calcium (Ca), magnesium-indium (Mg—In), magnesium-silver (Mg—Ag), silver-magnesium (Ag—Mg), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

The layers constituting the hole transport region 130 and the layers constituting the electron transport region 170 may be formed in a certain region by vacuum deposition, spin coating, casting, Langmuir-Blodgett (LB), ink-jet printing, laser-printing, and/or a laser induced thermal imaging (LITI).

When the layers constituting the hole transport region 130 and the layers constituting the electron transport region 170 are formed by deposition, the deposition may be performed at a deposition temperature of about 100° C. to about 500° C., at a vacuum degree of about $10^{-8}$ torr to about $10^{-3}$ torr, and at a deposition rate of about 0.01 nm/sec to about 100 nm/sec, depending on a material for forming a layer and the structure of each layer to be formed.

When the layers constituting the hole transport region 130 and the layers constituting the electron transport region 170 are formed by spin coating, the spin coating may be performed at a coating speed of about 2,000 rpm to about 5,000 rpm and at a heat treatment temperature of about 80° C. to about 200° C., depending on a material to be included in a layer and the structure of each layer to be formed.

Hereinafter, a light-emitting device according to one or more embodiments of the present disclosure will be described in further detail with reference to Examples, but the present disclosure is not limited thereto.

Preparation Example 1: Preparation of Perovskite Compound (Blue Light Emission) Represented by Formula 1

15 mL of octadecene, 3 mL of oleylamine, 1.5 mL of an oleic acid (OA), and a mixture including 0.2 g of $EuI_2$ (a molar ratio of 1:1) were added to a 100-ml four-neck flask. The reaction mixture was mixed at a temperature of 100° C. for 30 minutes and heated at a temperature of 150° C. to 170° C. for 10 minutes in an argon atmosphere.

Then, 0.55 mL of a cesium stearate (CsSt) solution (0.15 M ODE) was quickly added to the four-neck flask which was then rapidly cooled in an ice water tank after 5 seconds to obtain a (cube-shaped) $(CH_3NH_3)EuI_3$ nanoparticle.

Preparation Example 2: Preparation of First Quantum Dot (Red Light Emission)

Indium acetate, an oleic acid, and 1-octadecene (ODE) were added to a reaction container and mixed at a temperature of 120° C. for 1 hour in a vacuum atmosphere to obtain a first mixture. Then, zinc acetate, an oleic acid, and 1-octadecene (ODE) were added to a separate container and mixed at a temperature of 120° C. for 1 hour in a vacuum to obtain a second mixture. Then, the first mixture and the second mixture were added to a three-neck flask, and tris(trimethylsilyl)phosphine was added to the flask while heating the first mixture and the second mixture at a temperature of 300° C. in an argon atmosphere. As a result, an InP quantum dot (grain size=4.5 nm to 6 nm) was obtained. Then, the obtained InP quantum dot was purified by using methanol.

The InP quantum dot, trioctylphosphine oxide, and hexadecyl amine were added to a reaction container and heated to a temperature of 190° C. in an argon atmosphere. A mixture of zinc stearate, a sulfur powder, trioctylphosphine, and toluene, which was heated to a temperature of 100° C., was added to the reaction container at a speed of 0.1 ml/min. The mixture in the reaction container was stirred at a temperature of 190° C. for 1 hour. Then, the mixture was purified by using methanol to obtain an InP/ZnS quantum dot (first quantum dot; grain size=7 nm to 8 nm) having a ZnS shell.

Preparation Example 3: Preparation of Second Quantum Dot (Green Light Emission Indium acetate, an oleic acid, and 1-octadecene (ODE) were added to a reaction container and mixed at a temperature of 120° C. for 1 hour in a vacuum to obtain a first mixture. Then, zinc acetate, an oleic acid, and 1-octadecene (ODE) were added to another container and mixed at a temperature of 120° C. for 1 hour in a vacuum to obtain a second mixture. Then, the first mixture and the second mixture were added to a three-neck flask and tris(trimethylsilyl)phosphine was added to the flask while heating the first mixture and the second mixture at a temperature of 300° C. in an argon atmosphere. As a result, an InP quantum dot (grain size=2.5 nm to 3.5 nm) was obtained. Then, the obtained InP quantum dot was purified by using methanol.

The InP quantum dot, trioctylphosphine oxide, and hexadecyl amine were added to a reaction container and heated to a temperature of 190° C. in an argon atmosphere. A mixture of zinc stearate, a sulfur powder, trioctylphosphine, and toluene, which was heated to a temperature of 100° C., was added to the reaction container at a speed of 0.1 ml/min. The mixture in the reaction container was stirred at a temperature of 190° C. for 1 hour. Then, the mixture was purified by using methanol to obtain an InP/ZnS quantum dot (grain size=4 nm to 5 nm) having a ZnS shell.

Evaluation Example 1

Emission wavelengths of the perovskite compound represented by Formula 1, the first quantum dot, and the second quantum dot, which were obtained in Preparation Examples 1 to 3, were measured by using photoluminescence spectroscopy (PL), and results thereof are shown in Table 1.

TABLE 1

|  | Emission wavelength (nm) |
| --- | --- |
| Preparation Example 1 | 450 |
| Preparation Example 2 | 620 |
| Preparation Example 3 | 510 |

Referring to Table 1, it was confirmed that the perovskite compound represented by Formula 1, which was prepared in Preparation Example 1, emitted blue light, the first quantum dot prepared in Preparation Example 2 emitted red light, and the second quantum dot prepared in Preparation Example 3 emitted green light.

Preparation Example 4: Preparation of Composition 1 for Forming Emission Layer 0.035 g of the $(CH_3NH_3)EuI_3$ nanoparticle (perovskite compound represented by Formula 1) obtained in Preparation Example 1, 0.02 g of the InP/ZnS quantum dot (first quantum dot) obtained in Preparation Example 2, 0.01 g of the InP/ZnS quantum dot (second quantum dot) obtained in Preparation Example 3, and 2.5 ml of toluene were added to a 10-ml vial. The mixture was mixed at a temperature of 25° C. for 10 minutes to obtain Composition 1 for forming an emission layer.

Preparation Example 5: Preparation of Composition 2 for Forming Emission Layer Composition 2 for forming an emission layer was obtained in substantially the same manner as described with respect to Preparation Example 4, except that CdSe/ZnS (grain size=3 nm to 4 nm, emission wavelength: 450 nm) was used instead of the $(CH_3NH_3)EuI_3$ nanoparticle obtained in Preparation Example 1.

Example 1

Formation of Hole Transport Region

An ITO anode was prepared by cutting a glass substrate (manufactured by Corning), on which an ITO layer was deposited to a thickness of 10 Ω/cm² (150 nm), to a size of 50 mm×50 mm×0.5 mm, ultrasonically cleaning the glass substrate by using acetone, isopropyl alcohol, and pure water each for 15 minutes, and then, exposing the glass substrate to UV irradiation and ozone for 30 minutes to clean the glass substrate. Then, the glass substrate was loaded into a vacuum deposition apparatus.

PEDOT:PSS was deposited on the ITO anode to form a hole injection layer having a thickness of 25 nm, and poly-TPD was deposited on the hole injection layer to form a hole transport layer having a thickness of 25 nm, thereby forming a hole transport region.

Formation of Emission Layer

About 1 mL of Composition 1 for forming an emission layer, which was prepared in Preparation Example 4, was extracted and spin-coated on the hole transport region at a speed of 3,000 rpm for 20 seconds to form an emission layer having a thickness of 30 nm.

Formation of Electron Transport Region $Alq_3$ was deposited on the emission layer to form an electron transport layer having a thickness of 40 nm.

Formation of Cathode

LiF (2 nm):Al (100 nm) was deposited on the electron transport region to form a cathode having a thickness of 102 nm, thereby completing the manufacture of a light-emitting device having a structure of ITO (150 nm)/PEDOT:PSS (25 nm)/poly-TPD (25 nm)/$(CH_3NH_3)EuI_3$+InP/ZnS (grain size=7 nm to 8 nm)+InP/ZnS (grain size=4 nm to 5 nm) (30 nm)/$Alq_3$ (40 nm)/LiF:Al (2 nm:100 nm).

Comparative Example 1

A light-emitting device of Comparative Example 1 was manufactured in substantially the same manner as described with respect to Example 1, except that Composition 2 for forming an emission layer, which was prepared in Preparation Example 5, was used in forming an emission layer.

Evaluation Example 2

External quantum efficiency of the light-emitting device manufactured according to Example 1 was measured at 5 mA/cm² by using a Keithley SMU 236 and a luminance meter PR650, and results thereof are shown in Table 2.

TABLE 2

| | Composition of emission layer | | | External quantum efficiency (EQE) (%) |
|---|---|---|---|---|
| | Blue light emission | Red light emission | Green light emission | |
| Example 1 | $(CH_3NH_3)EuI_3$ | InP/ZnS (grain size = 7 nm to 8 nm) | InP/ZnS (grain size = 4 nm to 5 nm) | 20 |
| Comparative Example 1 | Cds/ZnSe (grain size = 3 nm to 4 nm) | InP/ZnS (grain size = 7 nm to 8 nm) | InP/ZnS (grain size = 4 nm to 5 nm) | 10 |

Referring to Table 2, it was confirmed that the light-emitting device of Example 1 had high external quantum efficiency, as compared with that of the light-emitting device of Comparative Example 1.

According to one or more embodiments, a light-emitting device may have high efficiency and/or a long lifespan.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure. In the drawing, the relative sizes of elements, layers, and regions may be exaggerated for clarity.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on" another element or layer, it can be directly on the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, acts, operations, elements, and/or components, but do not preclude the presence or addition of one or more other features, integers, acts, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively.

Also, the term "exemplary" is intended to refer to an example or illustration.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the accompanying drawing, it will be understood by those of ordinary skill in the art that various changes in form and details may be made therein without departing from the spirit and scope as defined by the following claims, and equivalents thereof.

What is claimed is:

1. A light-emitting device comprising:
a first electrode;
a second electrode facing the first electrode; and
an emission layer between the first electrode and the second electrode,
wherein the emission layer comprises at least one perovskite compound represented by Formula 1, a first quantum dot, and a second quantum dot, and
the first quantum dot and the second quantum dot are different from each other:

$$[A][B][X]_3 \quad \text{Formula 1}$$

wherein, in Formula 1,
A is at least one monovalent organic cation, at least one monovalent inorganic cation, or any combination thereof,
B is at least one divalent inorganic cation, and
X is at least one monovalent anion.

2. The light-emitting device of claim 1, wherein:
A is $(R_1R_2R_3R_4N)^+$, $(R_1R_2R_3R_4P)^+$, $(R_1R_2R_3R_4As)^+$, $(R_1R_2R_3R_4Sb)^+$, $(R_1R_2N=C(R_3)-NR_4R_5)^+$, a monovalent cation of a substituted or unsubstituted nitrogen-containing 5-membered ring, a monovalent cation of a substituted or unsubstituted nitrogen-containing 6-membered ring, $Li^+$, $Na^+$, $K^+$, $Rb^+$, $Cs^+$, $Fr^+$, or any combination thereof, and
$R_1$ to $R_5$, a substituent of the monovalent cation of the substituted nitrogen-containing 5-membered ring, and a substituent of the monovalent cation of the substituted nitrogen-containing 6-membered ring are each independently selected from hydrogen, deuterium, —F, —Cl, —Br, —I, a hydroxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_6$-$C_{60}$ aryl group, and —N$(Q_1)(Q_2)(Q_3)$, and
wherein $Q_1$ to $Q_3$ are each independently selected from hydrogen, deuterium, a hydroxyl group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_6$-$C_{60}$ aryl group.

3. The light-emitting device of claim 1, wherein:
A is $(R_1R_2R_3R_4N)^+$, $(R_1R_2R_3R_4P)^+$, $(R_1R_2R_3R_4As)^+$, $(R_1R_2R_3R_4Sb)^+$, or any combination thereof, and
$R_1$ to $R_4$ are each independently selected from hydrogen, deuterium, —F, —Cl, —Br, —I, a hydroxyl group, a $C_1$-$C_{20}$ alkyl group, a $C_1$-$C_{20}$ alkoxy group, and —N$(Q_1)(Q_2)(Q_3)$, and
wherein $Q_1$ to $Q_3$ are each independently selected from hydrogen, deuterium, a hydroxyl group, a $C_1$-$C_{20}$ alkyl group, and a $C_1$-$C_{20}$ alkoxy group.

4. The light-emitting device of claim 1, wherein:
A is $(CH_3NH_3)^+$, $(C_2H_6PH_2)^+$, $(CH_3AsH_3)^+$, $(NH_4)^+$, $(CH_3SbH_3)^+$, $(PH_4)^+$, $(PF_4)^+$, $(CH_3PH_3)^+$, $(SbH_4)^+$, $(AsH_4)^+$, $(NCl_4)^+$, $(NH_3OH)^+$, $(NH_3NH_2)^+$, $(CH(NH_2)_2)^+$, $(C_3N_2H_5)^+$, $((CH_3)_2NH_2)^+$, $(NC_4H_8)^+$, $((CH_3CH_2)NH_3)^+$, $((NH_2)_3C)^+$, or any combination thereof.

5. The light-emitting device of claim 1, wherein:
B is a divalent cation of a rare earth metal, a divalent cation of an alkali earth metal, or any combination thereof.

6. The light-emitting device of claim 1, wherein:
B is $La^{2+}$, $Ce^{2+}$, $Pr^{2+}$, $Nd^{2+}$, $Pm^{2+}$, $Eu^{2+}$, $Gd^{2+}$, $Tb^{2+}$, $Ho^{2+}$, $Er^{2+}$, $Tm^{2+}$, $Yb^{2+}$, $Lu^{2+}$, $Be^{2+}$, $Mg^{2+}$, $Ca^{2+}$, $Sr^{2+}$, $Ba^{2+}$, $Ra^{2+}$, $Pb^{2+}$, $Sn^{2+}$, or any combination thereof.

7. The light-emitting device of claim 1, wherein:
B is $Eu^{+2}$.

8. The light-emitting device of claim 1, wherein:
X is at least one halide anion.

9. The light-emitting device of claim 1, wherein:
X is $I^-$.

10. The light-emitting device of claim 1, wherein:
the first quantum dot has a core-shell structure that comprises a core comprising a first semiconductor nanocrystal and a shell surrounding the core and comprising a second semiconductor nanocrystal, and
the second quantum dot has a core-shell structure that comprises a core comprising a third semiconductor nanocrystal and a shell surrounding the core and comprising a fourth semiconductor nanocrystal.

11. The light-emitting device of claim 10, wherein:
the first semiconductor nanocrystal, the second semiconductor nanocrystal, the third semiconductor nanocrystal, and the fourth semiconductor nanocrystal each independently comprise a group II-VI element-containing compound semiconductor nanocrystal, a group III-V element-containing compound semiconductor nanocrystal, a group I-III-V element-containing compound semiconductor nanocrystal, a group I-II-III-V element-containing compound semiconductor nanocrystal, a group II-VI element-containing compound semiconductor nanocrystal doped with a rare earth element or a transition metal element, or any combination thereof.

12. The light-emitting device of claim 11, wherein:
the group II-VI element-containing compound semiconductor nanocrystal comprises ZnS, ZnSe, ZnTe, HgS, HgSe, HgTe, ZnSeS, ZnSeTe, ZnSTe, HgSeS, HgSeTe, HgSTe, HgZnS, HgZnSe, HgZnTe, HgZnSeS, HgZnSeTe, HgZnSTe, or any combination thereof, the group III-V element-containing compound semiconductor nanocrystal comprises GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, InAlPAs, or any combination thereof, the group I-III-V element-containing compound semiconductor nanocrystal comprises $CuInS_2$, $CuInSe_2$, or any combination thereof, the group I-II-III-V element-containing compound semiconductor nanocrystal comprises ZnCuInS, and the group II-VI element-containing compound semiconductor nanocrystal doped with the rare earth element or the transition metal element comprises Mn-doped ZnSe (Mn:ZnSe), Cu-doped ZnSe (Mn:ZnSe), Mn-doped ZnTe (Cu:ZnTe), Cu-doped ZnTe (Cu:ZnTe), or any combination thereof.

13. The light-emitting device of claim 10, wherein:
the first semiconductor nanocrystal comprises InP having a grain size of greater than about 4 nm and less than or equal to about 15 nm, $CuInS_2$ having a Cu-to-In atomic ratio of about 2:5 to about 8:5, ZnCuInS having a grain size of about 5 nm to about 10 nm, Mn-doped ZnSe (Mn:ZnSe)/ZnS, Mn-doped ZnTe (Mn:ZnTe), or any combination thereof,
the third semiconductor nanocrystal comprises InP having a grain size of about 2 nm to about 4 nm, $CuInS_2$ having a Cu-to-In atomic ratio of about 0.5:5 to about 2:5, ZnCuInS having a grain size of about 2 nm to about 5 nm, Cu-doped ZnSe (Cu:ZnSe), Cu-doped ZnTe (Cu:ZnTe), or any combination thereof, and
the second semiconductor nanocrystal and the fourth semiconductor nanocrystal each independently comprise ZnS.

14. The light-emitting device of claim 1, further comprising:
a hole transport region between the first electrode and the emission layer and an electron transport region between the emission layer and the second electrode,
wherein at least one selected from the hole transport region and the electron transport region independently comprises a metal halide, a metal oxide, a metal chalcogenide, a metal selenide, or any combination thereof.

15. The light-emitting device of claim 1, further comprising:
a hole transport region between the first electrode and the emission layer, and an electron transport region between the emission layer and the second electrode,
wherein at least one selected from the hole transport region and the electron transport region independently comprises a group IV element-containing compound semiconductor, a group III-V element-containing compound semiconductor, a group II-VI element-containing compound semiconductor, a group I-VII element-containing compound semiconductor, a group IV-VI element-containing compound semiconductor, a group V-VI element-containing compound semiconductor, a group II-V element-containing compound semiconductor, a ternary or quaternary compound semiconductor, or any combination thereof.

16. The light-emitting device of claim 1, further comprising:
at least one selected from a hole transport region between the first electrode and the emission layer; and an electron transport region between the emission layer and the second electrode,
wherein the hole transport region comprises an amine-based compound, and
wherein the electron transport region comprises a metal-free compound comprising at least one π electron-depleted nitrogen-containing ring.

17. The light-emitting device of claim 1, further comprising:
an electron transport region between the emission layer and the second electrode,
wherein the electron transport region comprises an electron injection layer, and
wherein the electron injection layer comprises an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combination thereof.

18. The light-emitting device of claim 1, wherein:
the perovskite compound emits a first color light,
the first quantum dot emits a second color light,
the second quantum dot emits a third color light,
an upper emission wavelength of the first color light, an upper emission wavelength of the second color light, and an upper emission wavelength of the third color light are identical to or different from one another, and
mixed light comprising the first color light, the second color light, and the third color light is emitted.

19. The light-emitting device of claim 18, wherein:
the upper emission wavelength of the first color light, the upper emission wavelength of the second color light, and the upper emission wavelength of the third color light are different from one another, and
the mixed light including the first color light, the second color light, and the third color light is white light.

20. The light-emitting device of claim 18, wherein:
the first color light is blue light, the second color light is red light, and the third color light is green light.

* * * * *